US00PP23444P2

(12) United States Plant Patent
Donahue

(10) Patent No.: US PP23,444 P2
(45) Date of Patent: Mar. 5, 2013

(54) ***LANTANA* PLANT NAMED 'ELEGET'**

(50) Latin Name: *Lantana camara*
Varietal Denomination: ELEGET

(76) Inventor: Mitch Donahue, Indian Trail, NC (US)

( * ) Notice: Subject to any disclaimer, the term of this patent is extended or adjusted under 35 U.S.C. 154(b) by 43 days.

(21) Appl. No.: 13/134,472

(22) Filed: Jun. 7, 2011

(51) Int. Cl.
*A01H 5/00* (2006.01)

(52) U.S. Cl. ..... Plt./227
(58) Field of Classification Search ..... Plt./227
See application file for complete search history.

*Primary Examiner* — Susan McCormick Ewoldt
(74) *Attorney, Agent, or Firm* — Cassandra Bright

(57) ABSTRACT

A new and distinct *Lantana* cultivar named 'ELEGET' is disclosed, characterized by a short, dense plant habit. The new variety is floriferous and produces light yellow flowers held just above the top of the canopy of the plant. Inflorescence is less spherical than typical *Lantana* inflorescence. The new variety is a *Lantana*, normally produced as an outdoor garden or container plant.

3 Drawing Sheets

Latin name of the genus and species: *Lantana camara*.
Variety denomination: 'ELEGET'.

BACKGROUND OF THE INVENTION

The new *Lantana* cultivar is a product of a planned breeding program conducted by the inventor, Mitch Donahue. The objective of the breeding program was to produce new *Lantana* varieties for ornamental commercial applications. The cross resulting in this new variety was made during August 2009 at a commercial nursery in Indian Trail, N.C.

The seed parent is the unpatented, proprietary seedling variety referred to as *Lantana camara* '0603' The pollen parent is the unpatented proprietary seedling variety referred to as *Lantana camara* '0623'. The new variety was discovered in Jun. 1, 2010 by the inventor in a trial field of seedlings resulting from the 2009 crossing, at a commercial nursery in Indian Trail, N.C.

Asexual reproduction of the new cultivar 'ELEGET' by vegetative cuttings was first performed at a research greenhouse in Indian Trail, N.C. in June 2010. Subsequently, at least 5 generations have been produced, and have shown that the unique features of this cultivar are stable and reproduced true to type in successive generations.

SUMMARY OF THE INVENTION

The cultivar 'ELEGET' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ELEGET' These characteristics in combination distinguish 'ELEGET' as a new and distinct *Lantana* cultivar:

1. Very Short, dense plant habit
2. Light yellow flower color
3. Very floriferous
4. Corymb type flower is less spherical than typical *lantana*
5. Flowers are held attractively tight on top canopy of plant
6. Continuous flowering.

Plants of the new cultivar 'ELEGET' are similar to plants of the seed parent, *Lantana camara* '0603' in most horticultural characteristics, however, plants of the new cultivar 'ELEGET' are much shorter, and produce a different color yellow flower. Additionally, plants of the seed parent produce overall larger plants, leaves and inflorescences.

Plants of the new cultivar 'ELEGET' are similar to plants of the pollen parent, *Lantana camara* '0623' in most horticultural characteristics, however, plants of the new cultivar 'ELEGET' produce, smaller flowers and leaves. Additionally, the new variety produces softer yellow colored flowers, and overall much shorter plants.

COMMERCIAL COMPARISON

Plants of the new cultivar 'ELEGET' are comparable to the variety *Lantana camara* 'Sunglow' unpatented. The two *Lantana* varieties are similar in most horticultural characteristics however, the new variety 'ELEGET' differs in having softer yellow flowers, than the comparator variety. Additionally 'ELEGET' produces much smaller flowers, foliage than 'Sunglow'. Plants of 'ELEGET' have an overall much shorter plant habit than 'Sunglow'.

Plants of the new cultivar 'ELEGET' are comparable to the unpatented variety *Lantana* 'Simon Yellow'. The two *Lantana* varieties are similar in most horticultural characteristics however, plants of the new variety 'ELEGET' are much shorter and more floriferous than 'Simon Yellow'.

BRIEF DESCRIPTION OF THE PHOTOGRAPHS

The accompanying photograph in FIG. 1 illustrates in full color a typical plant of 'ELEGET' grown in a greenhouse, in a 1 gallon pot. Age of the plant photographed is approximately 16 weeks from a rooted cutting.

Figure 1:
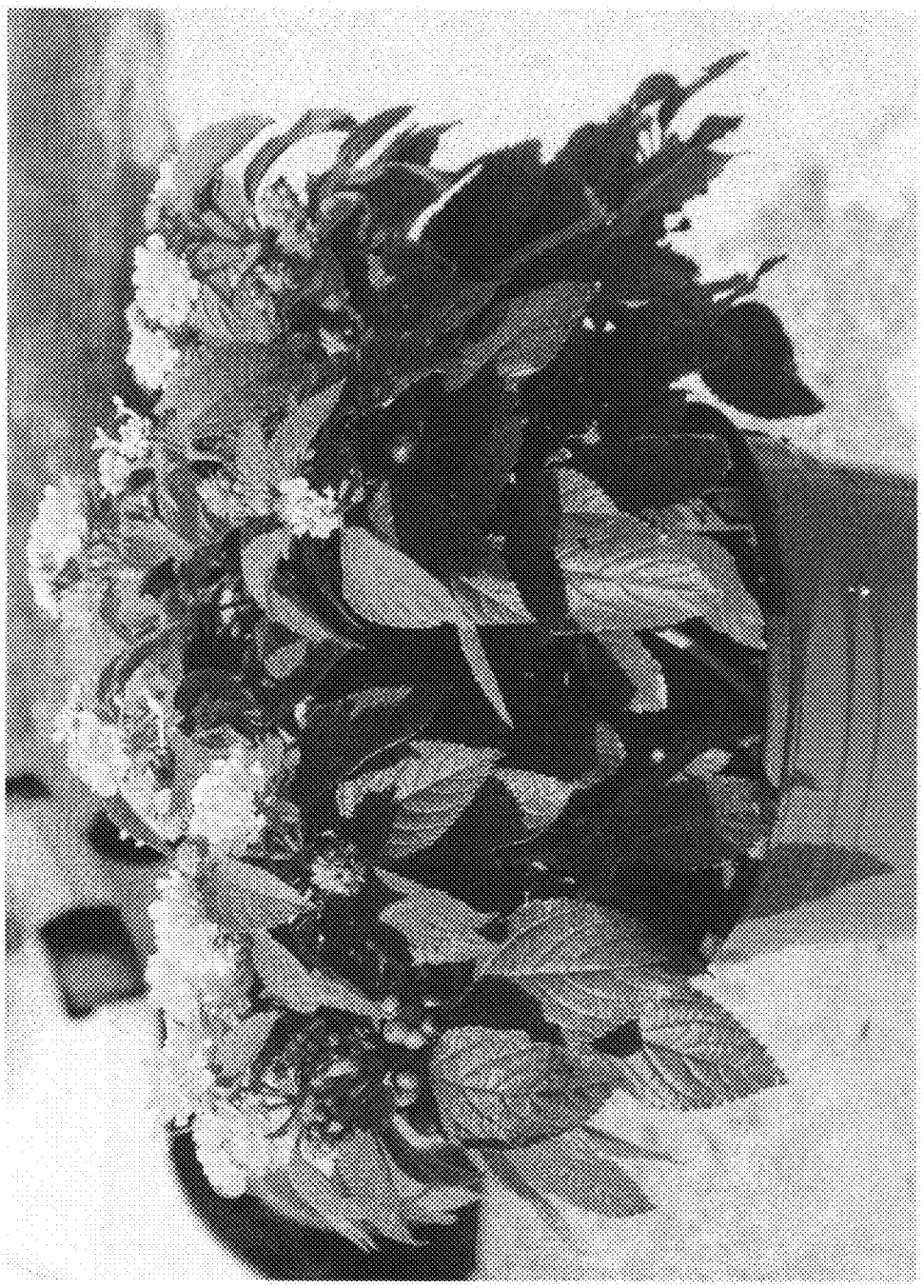
Figure 2:
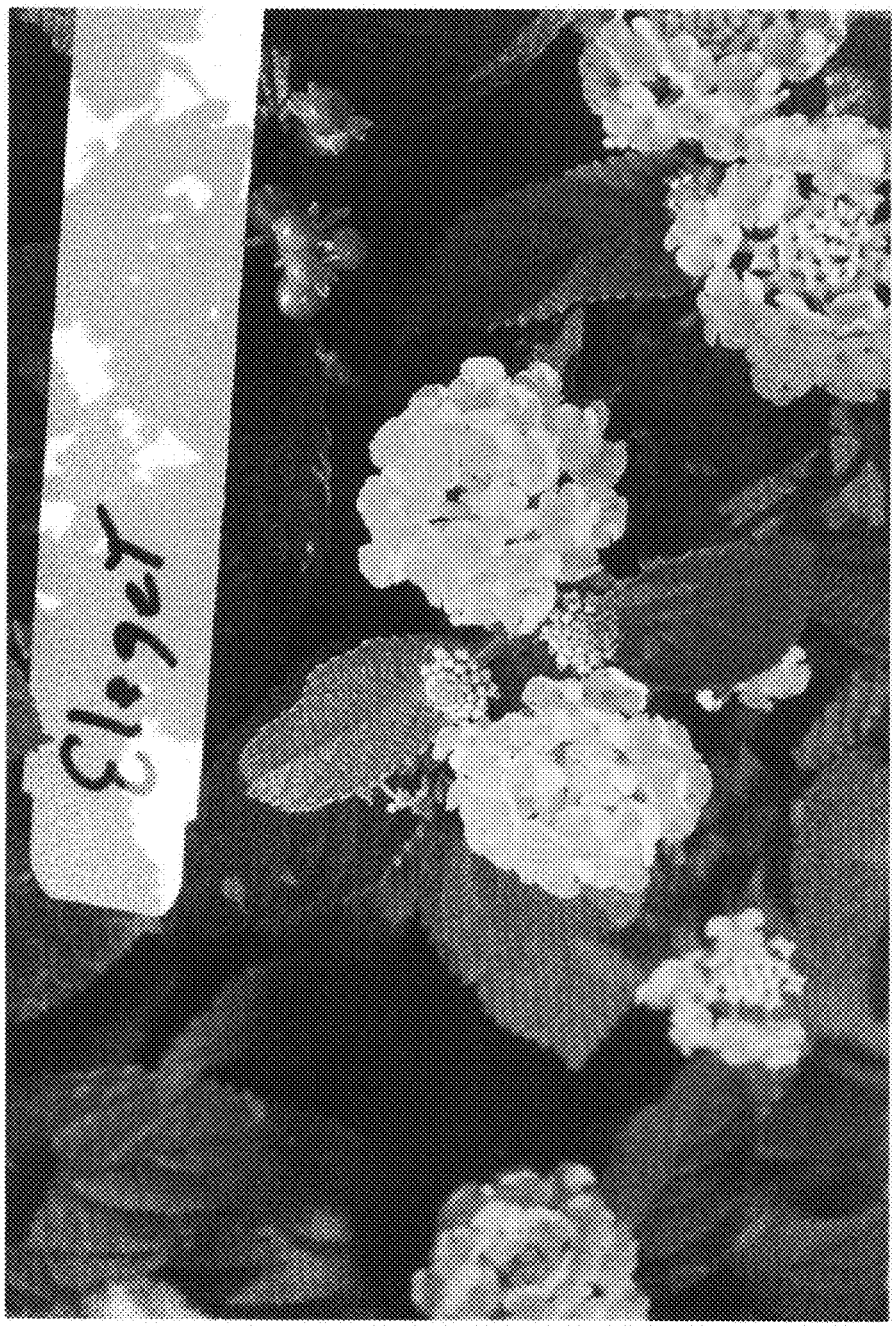
FIG. 2 illustrates in full color a close up of a typical inflorescence of 'ELEGET'.
Figure 3:
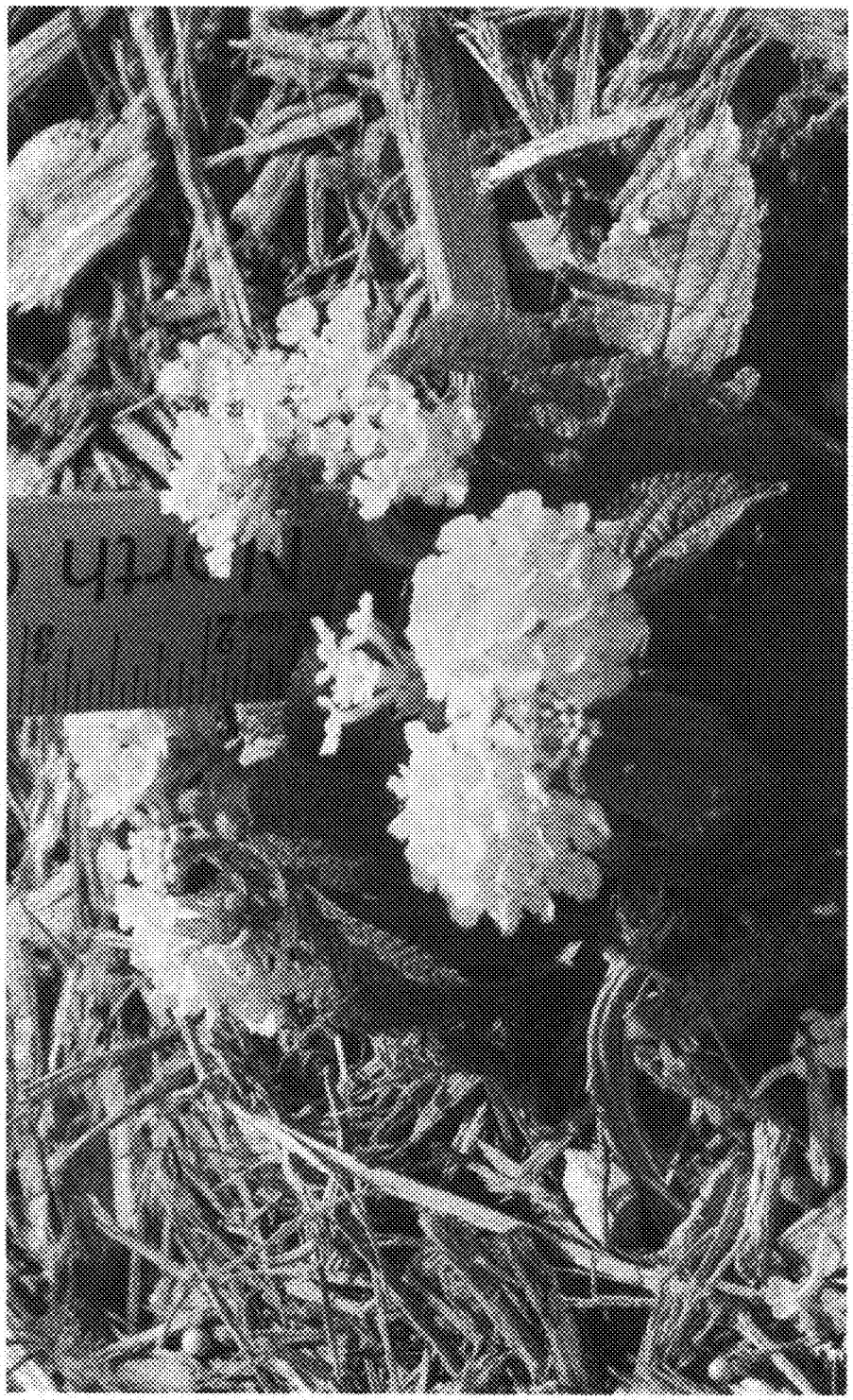
FIG. 3 is a 10 week old plant, grown outdoors in the ground in North Carolina.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ELEGET' plants grown 10 weeks in greenhouse, then 6 weeks outdoors during spring in Indian Trail, N.C. The growing temperature ranged from 10° C. to 15° C. during the night and from 22° C. to 34° C. during the day. General light conditions are bright, normal sunlight. Measurements and numerical values represent averages of typical plant types. Botanical classification: *Lantana camara* 'ELEGET'.

PROPAGATION

Time to initiate roots: 10 to 14 days at approximately 15° C.
Root description: Fibrous.

PLANT

Age of plant described: Approximately 112 days from a rooted cutting.
Growth habit: Upright/Mounding.
Pot size of plant described: 1 Gallon (15 cm) Pot.
Height: Approximately 24 cm.
Plant spread: Average 26-28 cm.
Growth rate: Medium vigor.
Branching characteristics: Free branching.
Length of primary lateral branches: 14 cm.
Diameter of lateral branches: 0.1 cm.
Quantity of primary lateral branches: 2 main and 2 at each node.
Characteristics of primary lateral branches:
- *Form*.—Square Stem.
- *Diameter*.—0.1 cm.
- *Color*.—Near RHs Yellow-Green 144A.
- *Texture*.—Light to Moderate Pubescence.
- *Strength*.—Strong.

Internode length: Average 1.6 cm.

FOLIAGE

Leaf:
- *Arrangement*.—Opposite.
- *Quantity*.—Approximately 12-14 per branch.
- *Average length*.—6 cm.
- *Average width*.—3.6 cm.
- *Shape of blade*.—Ovate.
- *Apex*.—Pointed.
- *Base*.—Pointed.
- *Margin*.—Serrated.
- *Texture of top surface*.—Scabrous.
- *Pubescence*.—Covered with hairs.
- *Color*.—Young foliage upper side: Near RHS Yellow-Green 144C. Young foliage under side: Near RHS Yellow-Green 144D. Mature foliage upper side: Near RHS Green 137A. Mature foliage under side: Near RHS Green 138B.
- *Venation*.—Type: Pinnate. Venation color upper side: Young Foliage: Near RHS Green 140A. Mature Foliage: Near RHS Greyed-Green 192A. Venation color under side: Young Foliage: Near RHS Yellow-Green 146B. Mature Foliage: Near RHS Yellow-Green 144B.
- *Petiole*.—Length: Approximately 1.6 cm. Diameter: Approximately 0.2 cm. Color: Near RHS Green 141C. Texture: Moderately covered with stiff hairs.

FLOWER

Natural flowering season: Spring-Fall or Year Round in Warm Climate.
Days to flowering from rooted cutting: 28.
Inflorescence and flower type and habit: Corymb.
Rate of flower opening: 1 to 2 days from bud to fully opened flower.
Flower longevity on plant: 5 days from mature age bloom.
Persistent or self-cleaning: Self Cleaning.
Flower fragrance: Light.
Bud:
- *Shape*.—Rectangular.
- *Length*.—0.2 cm.
- *Diameter*.—0.3 cm.
- *Color*.—Near RHS Yellow 11C darkens to 11A before opening.

Overall inflorescence size:
- *Height*.—Approximately 1.6 cm.
- *Diameter*.—Approximately 3 cm.

Individual flower size:
- *Height*.—Approximately 1.4 cm, including Corolla Tube, Corolla tube length 1 cm.
- *Diameter*.—Approximately 0.9 cm.

Corolla:
- *Petals/lobes*.—Number: 5 — 2 top lobes are fused almost to appear as 1 lobe. All 5 are formed at base to form a corolla tube. Length: 0.4 cm — upper, 0.4 cm — lateral, 0.6 cm — lower. Width: 0.3 cm — upper, 0.3 cm — lateral, 0.5 cm — lower. Shape: Obovate. Aspect: Slightly Rounded — Cupped. Margin: Entire — Faintly Ruffled. Texture: Smooth. Color: When opening: Upper surface: Near RHS Yellow 9A. Lower surface: Near RHS Yellow 9D. Fully opened: Upper surface: Near RHS Yellow 9A and 9C. Lower surface: Near RHS Yellow 9D.
- *Throat/tube*.—Color: Inner Near RHS Yellow 8A: Outer Yellow 10C. Texture: Smooth inner and outer at base end becoming slightly pubescent at top.
- *Tube color*.—Near RHS Yellow 10C.

Calyx/sepals:
- *Form*.—Fused To Form Calyx.
- *Length*.—0.2 cm.
- *Diameter*.—0.1 cm.
- *Sepal shape*.—Curved.
- *Sepal margin*.—Fused.
- *Sepal texture*.—Smooth.
- *Sepal color*.—Upper surface: Near RHS Yellow-Green 145D. Lower surface: Near RHS Yellow-Green 145D.

Flower bracts/inflorescence bracts:
- *Quantity*.—One per flower.
- *Aspecte*.—Slightly Cupped.
- *Length*.—Approximately 0.5 cm.
- *Width*.—Approximately 0.1 cm.
- *Shape*.—Lanceolate.
- *Apex*.—Acute.
- *Margin*.—Entire.

*Texture*.—Inner and outer surfaces: Pubescent.
*Color*.—Both surfaces: Near RHS Green 142B, Brown 200A at tip.

Peduncles:
*Length*.—Approximately 2.2 cm.
*Diameter*.—Approximately 0.1 cm.
*Angle*.—About 45 degrees.
*Strength*.—Strong.
*Texture*.—Smooth.
*Color*.—Near RHS Yellow-Green 144A.

REPRODUCTIVE ORGANS

Stamens:
*Number* (*per flower*).—4.
*Filaments*.—Not present.
*Anthers*.—Shape: Linear. Length: approx 0.1 cm. Color: Near RHS Brown 200D.

Pollen:
*Color*.—Near RHS Yellow 4C.
*Amount*.—Sparse.

Pistils:
*Quantity per flower*.—1.
*Length*.—0.3 cm.
*Style*.—Length: 1.5 mm. Color: Near RHS Greyed-Orange 177B.
*Ovary color*.—Near Green 142B.
*Stigma*.—Shape: Oval. Color: Near RHS Green 142B.

OTHER CHARACTERISTICS

Seeds and fruits: Seed Diameter: 3 mm. Color: Near RHS Brown 200A. Seed Quantity: Sparse.

Disease/pest resistance: Neither resistance nor susceptibility to pathogens and pests common to *Lantana* have been observed.

Temperature tolerance: The new variety tolerates temperatures between 0 to 40° C.

What is claimed is:

1. A new and distinct cultivar of *Lantana* plant named 'ELEGET' as herein illustrated and described.

* * * * *